US006400837B2

(12) United States Patent
Souluer

(10) Patent No.: US 6,400,837 B2
(45) Date of Patent: Jun. 4, 2002

(54) LOCATION HEAD FOR AN APPARATUS FOR DETECTING VERY SMALL BREAST ANOMALIES

(75) Inventor: Farid Souluer, Exton, PA (US)

(73) Assignee: UltraTouch Corporation, Paoli, PA (US)

( * ) Notice: Subject to any disclaimer, the term of this patent is extended or adjusted under 35 U.S.C. 154(b) by 0 days.

(21) Appl. No.: 09/876,570

(22) Filed: Jun. 7, 2001

Related U.S. Application Data

(60) Division of application No. 09/241,193, filed on Feb. 1, 1999, which is a continuation-in-part of application No. 08/957,648, filed on Oct. 24, 1997, now Pat. No. 6,192,143.

(51) Int. Cl.$^7$ ............................................... G06K 9/00
(52) U.S. Cl. ..................................................... 382/128
(58) Field of Search ................................ 382/128, 325; 378/37; 128/915, 920; 33/511; 376/122, 123, 138, 339, 340, 609, 624; 348/77, 345, 350, 352

(56) References Cited

U.S. PATENT DOCUMENTS

| | | | |
|---|---|---|---|
| 3,498,114 A | 3/1970 | Garber et al. .................. | 73/649 |
| 3,933,148 A | 1/1976 | Wyler et al. ................ | 600/557 |
| 3,965,727 A | 6/1976 | Argabrite ........................ | 73/81 |
| 4,159,640 A | 7/1979 | Leveque et al. ................ | 73/81 |
| 4,250,894 A | 2/1981 | Frei ............................ | 600/587 |
| 4,257,705 A | * 3/1981 | Hosoe et al. ............... | 356/3.07 |
| 4,286,602 A | * 9/1981 | Guy ........................... | 600/476 |
| 4,407,292 A | * 10/1983 | Edrich ......................... | 600/430 |
| 4,930,872 A | * 6/1990 | Convery ..................... | 359/896 |
| 4,984,575 A | * 1/1991 | Uchiyama et al. ............. | 60/439 |

(List continued on next page.)

FOREIGN PATENT DOCUMENTS

| | | | | |
|---|---|---|---|---|
| DE | 3900561 A1 | 7/1990 | .......... | A61B/5/103 |
| DE | 43 43 612 A1 | 6/1995 | ............ | G01N/3/42 |
| EP | 0244 274 A1 | 11/1987 | ............ | A61B/5/10 |
| GB | 2173896 A | 10/1986 | .......... | G01N/21/47 |
| GB | 2206791 A | 1/1989 | ........... | A61B/10/00 |
| WO | WO 97/31573 A1 | 9/1997 | ............ | A61B/8/12 |

OTHER PUBLICATIONS

Koreska, J. and Smith, J.M., Portable Desktop Computer–Aided Digitiser System for the analysis of Spinal Deformities; Medical & Biological Engineering, Nov. 1982, pp. 715–726.

Cook et al., IEEE Transactions on Biochemical Engineering, Apr. 1981, vol. BME–28; pp. 366–371.

Sarvazyan, A.; Mechanical Imaging: A New Technology For Medical Diagnostics; International Journal of Medical Informatics; 1988, vol. 49, pp. 195–216.

Sarazyan et al., Mechanical Introscopy—A New Modality of Medical Imaging for Detection of Breast and Prostrate Cancer, Proc. of the 8$^{th}$ Symposium on Computer Based Medical Systems, Jun. 9–10, 1995, pp. 4–5.

Primary Examiner—Andrew W. Johns
Assistant Examiner—Shervin Nakhjavan
(74) Attorney, Agent, or Firm—Saul Ewing LLP; Alfred W. Zaher; Bruce D. George

(57) ABSTRACT

A computer controlled apparatus for detecting breast tumors by mechanically palpating a breast in a full scan manner to detect small lumps or anomalies. The patient is positioned on a fully adjustable bed and oriented relative to the apparatus. A detection head mounted for movement in three dimensions is positioned above the bed. A palpation finger is brought into pressure contact with a sequence of small areas across the entire breast, palpating each area to measure tissue density. Concurrent with the palpation scan, a scan of breast color and temperature is conducted. A locator head positions the detector for the scan in a manner that assures repeatability during each of a series of periodic examinations. This system detects very small lumps and allows easy, accurate monitoring of suspicious areas over an extended time period. Several different embodiments of the detection head and location head are described.

22 Claims, 8 Drawing Sheets

U.S. PATENT DOCUMENTS

| | | | |
|---|---|---|---|
| 5,078,142 A | 1/1992 | Siczek et al. | 600/407 |
| 5,079,698 A | 1/1992 | Grenier et al. | 382/128 |
| 5,107,837 A | 4/1992 | Ophir et al. | 600/437 |
| 5,122,644 A * | 6/1992 | Hasegawa et al. | 235/462 |
| 5,225,886 A * | 7/1993 | Koizumi et al. | 356/237 |
| 5,265,612 A | 11/1993 | Sarvazyan et al. | 600/471 |
| 5,301,681 A | 4/1994 | DeBan et al. | 600/549 |
| 5,320,111 A * | 6/1994 | Livingston | 600/567 |
| 5,361,767 A | 11/1994 | Yukov | 600/447 |
| 5,432,544 A * | 7/1995 | Ziarati | 600/410 |
| 5,465,722 A | 11/1995 | Fort et al. | 600/447 |
| 5,508,825 A * | 4/1996 | Kataoka | 358/474 |
| 5,519,198 A * | 5/1996 | Plesko | 235/462 |
| 5,524,636 A | 6/1996 | Saravazyan et al. | 600/587 |
| 5,568,811 A | 10/1996 | Olstad | 600/443 |
| 5,632,276 A | 5/1997 | Eidelberg et al. | 600/414 |
| 5,657,760 A | 8/1997 | Ying et al. | 600/439 |
| 5,706,822 A | 1/1998 | Khavari | 600/483 |
| 5,730,146 A | 3/1998 | Itil et al. | 600/545 |
| 5,733,739 A | 3/1998 | Zakim et al. | 435/29 |
| 5,749,364 A | 5/1998 | Sliwa, Jr. et al. | 600/438 |
| 5,779,634 A | 7/1998 | Ema et al. | 600/407 |
| 5,833,633 A | 11/1998 | Saravazyan et al. | 600/587 |
| 5,833,634 A | 11/1998 | Laird et al. | 600/587 |
| 5,860,934 A | 1/1999 | Saravazyan | 600/587 |
| 5,879,312 A | 3/1999 | Imoto | 600/587 |
| 5,922,018 A | 7/1999 | Sarvazyan | 600/587 |
| 5,940,802 A | 8/1999 | Hildebrand et al. | 705/3 |
| 5,957,866 A | 9/1999 | Shapiro et al. | 600/586 |
| 5,989,199 A | 11/1999 | Cundari et al. | 600/587 |
| 6,005,911 A | 12/1999 | Cheung | 378/37 |
| 6,015,384 A | 1/2000 | Ramamurthy et al. | 600/440 |
| 6,031,930 A | 2/2000 | Bacus et al. | 382/133 |
| 6,032,678 A | 3/2000 | Rottem | 600/437 |
| 6,055,452 A | 4/2000 | Pearlman | 600/547 |
| 6,056,690 A | 5/2000 | Roberts | 600/300 |
| 6,058,322 A | 5/2000 | Nishikawa et al. | 600/408 |
| 6,091,981 A | 7/2000 | Cundari et al. | 600/407 |
| 6,099,471 A | 8/2000 | Torp et al. | 600/438 |
| 6,113,540 A | 9/2000 | Iliff | 600/300 |
| 6,179,790 B1 | 1/2001 | Cundari et al. | 600/587 |
| 6,186,962 B1 | 2/2001 | Lloyd | 600/587 |
| 6,190,334 B1 | 2/2001 | Lasky | 600/587 |

* cited by examiner

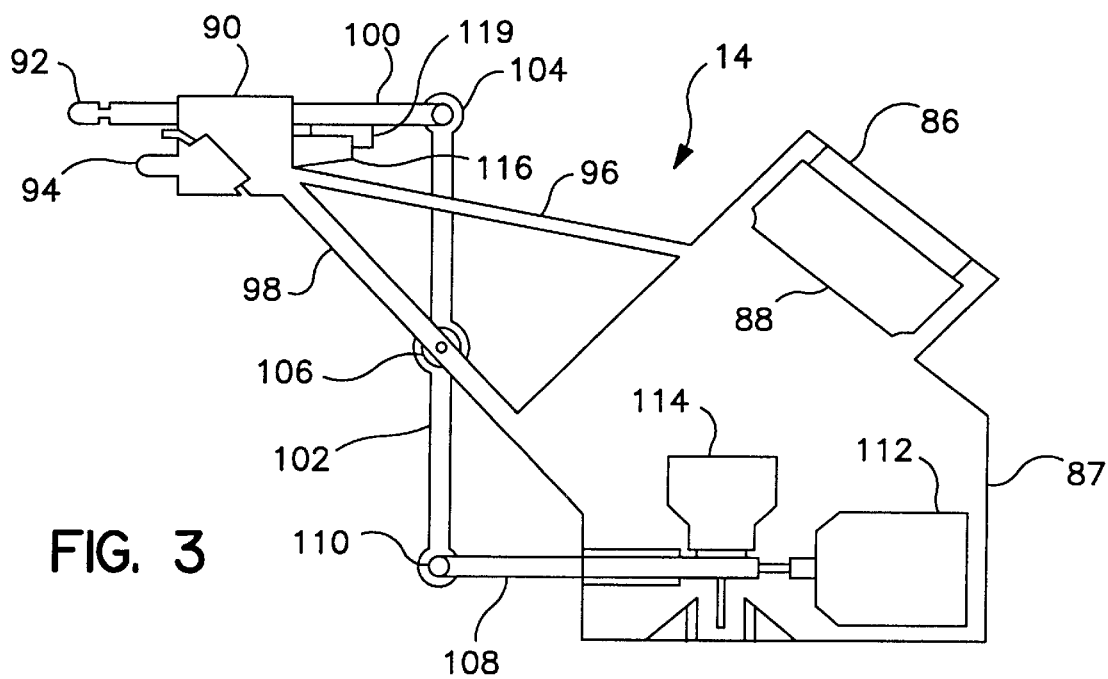
FIG. 3
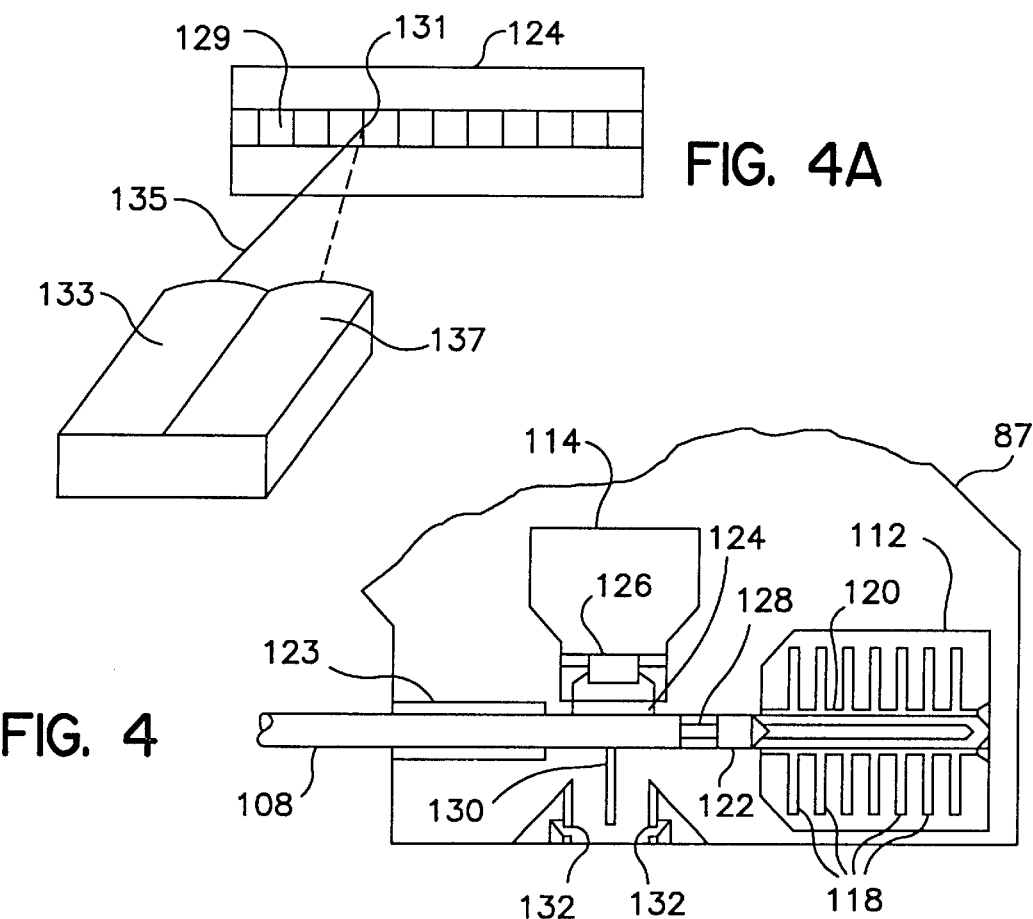
FIG. 4A
FIG. 4

LOCATION HEAD FOR AN APPARATUS FOR DETECTING VERY SMALL BREAST ANOMALIES

RELATED APPLICATIONS

This application is a division of applicant's copending U.S. patent application Ser. No. 09/241,193, filed Feb. 1, 1999, entitled "Apparatus for Detecting Very Small Breast Anomalies", which application is a continuation-in-part of U.S. patent application Ser. No. 08/957,648, filed Oct. 24, 1997, now U.S. Pat. No. 6,192,143, dated Feb. 20, 2001.

FIELD OF THE INVENTION

This invention relates to apparatus and methods for detecting very small anomalous masses, in particular tumors, in the human breast. In particular, this invention relates to detection heads for physically detecting breast anomalies and generating an electrical signal corresponding to changes in breast characteristics due to such anomalies.

BACKGROUND OF THE INVENTION

Recent findings indicate that one of eight women will develop breast cancer, the second leading cause of cancer death in women. Unopposed estrogen activity is an important pathogenic factor, with other risk factors including nulliparity, early menarche, late menopause, a family history of breast cancer, middle age and prior breast cancer.

The earliest indication of breast cancer generally is the occurrence of a painless lump, sometimes associated with nipple discharge and skin retraction. Later symptoms are generally due to metastases to bone, brain, lungs and liver. Early diagnosis may be possible through monthly self-examinations. Mammography has proven beneficial in early detection.

When a very small lump, <2 cm, is detected, a biopsy is generally performed, followed by treatment when the lump is found to be malignant. This can range from a lumpectomy with possible radiation treatment of axillary nodes to a modified radical mastectomy with axillary node dissection. With early treatment, the five-year survival rate is about 85%. Without early detection, if distant metastasis occur, the survival rate may drop to 10% or less.

Early detection of lumps is thus essential. Monthly self-examinations are very desirable, followed by examination by a physician if any suspicious areas are detected. It is, however, difficult for an unskilled person to detect very small lumps or to do a thorough examination.

Periodic palpation of the breasts by a physician and mammography will often detect very small tumors. These examinations should be reasonably frequent, particularly in older women, in order to detect tumors before they can metastasize. However the cost of frequent examinations, plus the accumulated radiation exposure from frequent mammograms tend to limit frequency. In addition, mammography may miss very small tumors, especially in the dense breasts of younger women. Further, pregnant women should avoid exposure to radiation.

Palpation of breasts will not detect very small changes and anomalies of the breast until the changes are so large or hard compared to the normal breast tissue that the difference can be detected by a touch of a finger. Generally, palpation is only capable of detecting changes where the anomalous tissue is relatively hard, has a diameter of at least about one centimeter and is close to the surface of the skin. Deeper anomalies, particular in large breasts, are difficult to detect by palpation. Since the characteristics of anomalies are not quantifiable, detecting changes in anomalies from one examination to another is difficult.

Thus, there is a continuing need for improved methods and apparatus for very early detection of very small breast anomalies that could be malignant, while avoiding radiation exposure.

SUMMARY OF THE INVENTION

The above-noted problems, and others, are overcome in accordance with this invention by an anomalies detection apparatus for thoroughly palpating entire breasts in a continuous, automatic scanning manner, to detect changes in breast tissue physical characteristics. In particular density is measured across the entire breast and, where anomalies are detected, mobility and size of the anomaly are measured.

The overall system of this detection apparatus includes a bed upon which the patient lies face up and which includes means for precisely positioning the patient in the same position for each of a series of periodic examinations. The detection head is mounted on a carriage for movement in three dimensions adjacent to a patient on the bed. A locator head associated with the detection head controls the bed positioning means to position the breasts in precisely the same position as for prior examinations. A palpation means on the detection head includes at least one finger-like palpation end movable toward and away from the breast surface to palpate the breast in the same general manner as a physician. The palpation device is preferably mounted so as to be movable across the entire breast surface sequentially while maintaining the finger generally perpendicular to the breast surface.

Information sensed by the palpation device is collected, stored and displayed in a conventional manner, such as is done with information from other systems such as computerized tomography and magnetic resonance imaging. The display will reveal, and show details of, any anomalies detected, so that further testing, such as through a biopsy, can be done.

BRIEF DESCRIPTION OF THE DRAWING

Details of the invention, and of preferred embodiments thereof, will be further understood upon reference to the drawings, wherein:

FIG. 3 is a schematic elevation view of a detection head and actuator;

FIG. 4 is a schematic elevation view of a detection head and actuator positioning device;

FIG. 4a is a schematic representation of a laser transmitter and receiver reading a laser card within a laser reader of the anomaly detection apparatus;

FIG. 13b is a schematic representation of a second embodiment of the encoder slide assembly shown in FIG. 13a;

DETAILED DESCRIPTION OF PREFERRED EMBODIMENTS

Figure 1:
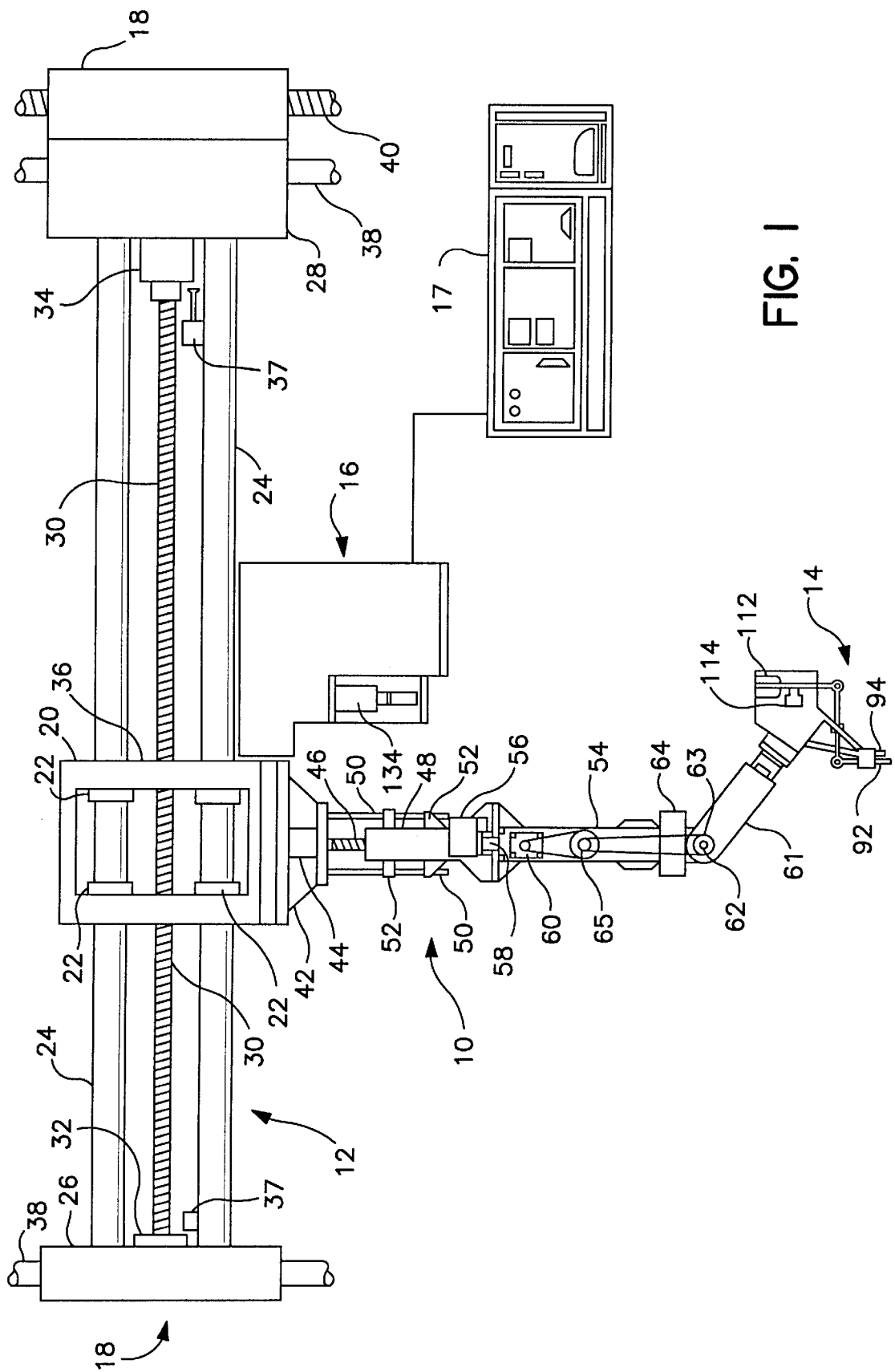
FIG. 1 is a schematic elevation view of an entire anomaly detection apparatus.

Referring to FIG. 1 there is seen a carriage 10 mounted at a proximal end on a horizontal support 12 for movement therealong. A detection head 14 (as detailed in FIGS. 3 and 4) is mounted at the distal end of carriage 10. A locator head 16 (detailed in FIG. 5) is also mounted to the carriage 10 for movement therewith. Digital information from and to detection head 14, locator head 16 and control commands to various motors, limit switches and the like are passed between a computer center 17 as schematically indicated. Information is received, stored, interpreted and displayed in the same manner as other medical scanning devices, such as CAT scans, MRI scans, etc. Three dimensional images can be viewed on a conventional computer monitor.

If desired, images may be shown with different tissue density areas shown in different colors. Artificial intelligence techniques may be used to improve system performance. The combination of tissue density information as developed by palpation and the ancillary local color and temperature information results in detection of much smaller tumors and the ability to easily track changes in discrete tissue areas.

Horizontal support 12 is mounted on a vertical support mechanism 18 (as detailed in FIG. 6) along which support 12 can move in a vertical direction. Horizontal support includes a traveler 20 that rides in bearings 22 along rods or tubes 24 that are secured at their ends to end blocks 26 and 28. A lead screw 30 extends from a bearing 32 at end block 26 to a drive motor 34 at end block 28. Lead screw 30 extends through correspondingly threaded openings in walls 36 of traveler 20 so that traveler 20 will move to the right or left as the lead screw 30 is rotated in one direction or the other. Conventional limit switches 37 prevent over travel of traveler 20.

Guide rods 38 extend vertically through end blocks 26 and 28 and a lead screw 40 extends vertically through end block 28. These components are shown completely and discussed in conjunction with the discussion of FIG. 6, below.

Carriage 10 includes a base 42 secured to traveler 20. A motor 44 within base 42 rotates a screw 46 that is threaded into an intermediate body 48 to raise and lower the intermediate body 48 as the screw 46 is rotated one way or the other. A pair of guide rods 50 extend through brackets 52 to guide movement of the intermediate body 48. A lower body 54 is secured to intermediate body 48 for rotation relative thereto. A motor 56 is mounted on intermediate body 48 with lower body 54 mounted on the motor shaft 58 for rotation with the shaft.

An arm 61 is pivotally mounted at pivot 62 on bracket 64 mounted on the distal end of lower body 54. A motor 60 on lower body 54 drives a pulley 63 on arm 61 through a jackshaft 65.

Figure 6:
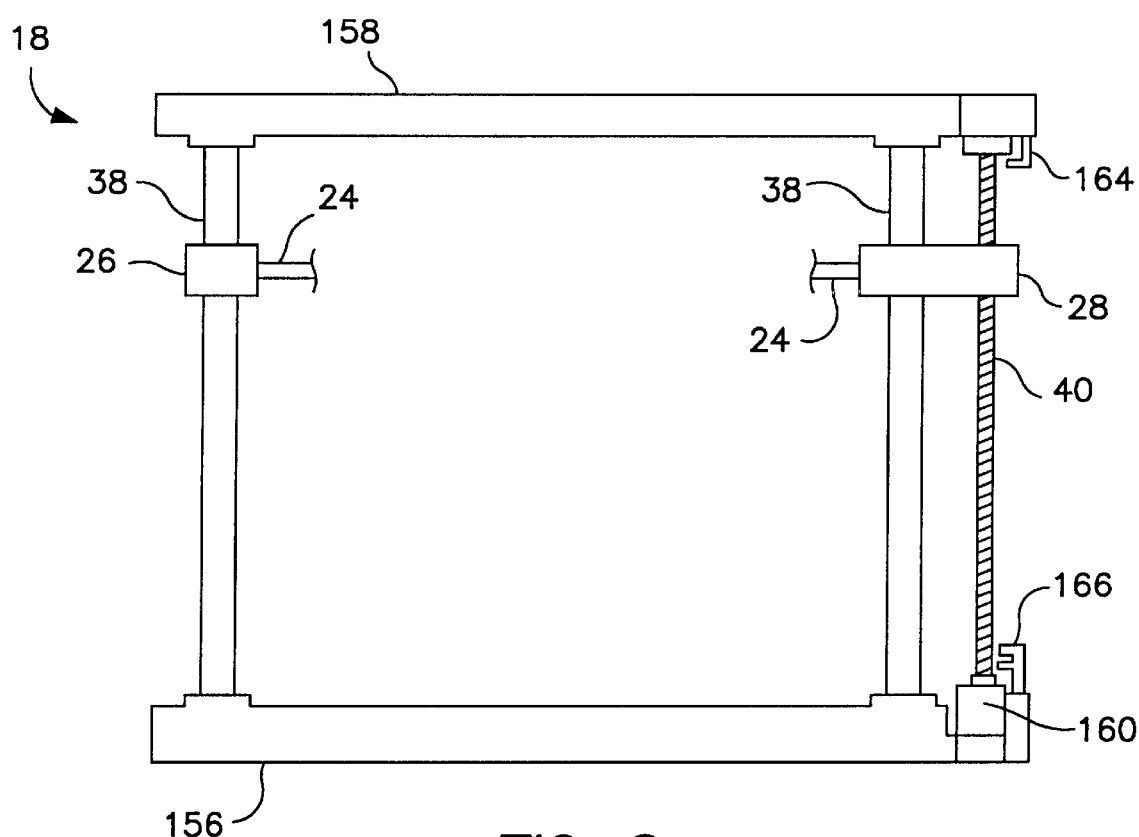
FIG. 6 is a schematic elevation view of a vertical positioning mechanism of the anomaly detection apparatus of FIG. 1.

Thus, the entire carriage 10 can be moved horizontally by horizontal support 12 and vertically by the vertical support 18 of FIG. 6. Lower body 54 of the carriage 10 can be rotated through a full circle. Arm 61 carrying detection head 14 can be pivoted through at least 180°. This combination of movements permits the detection 14 head to be positioned in any desired position relative to any portion of a breast surface.

Figure 2:
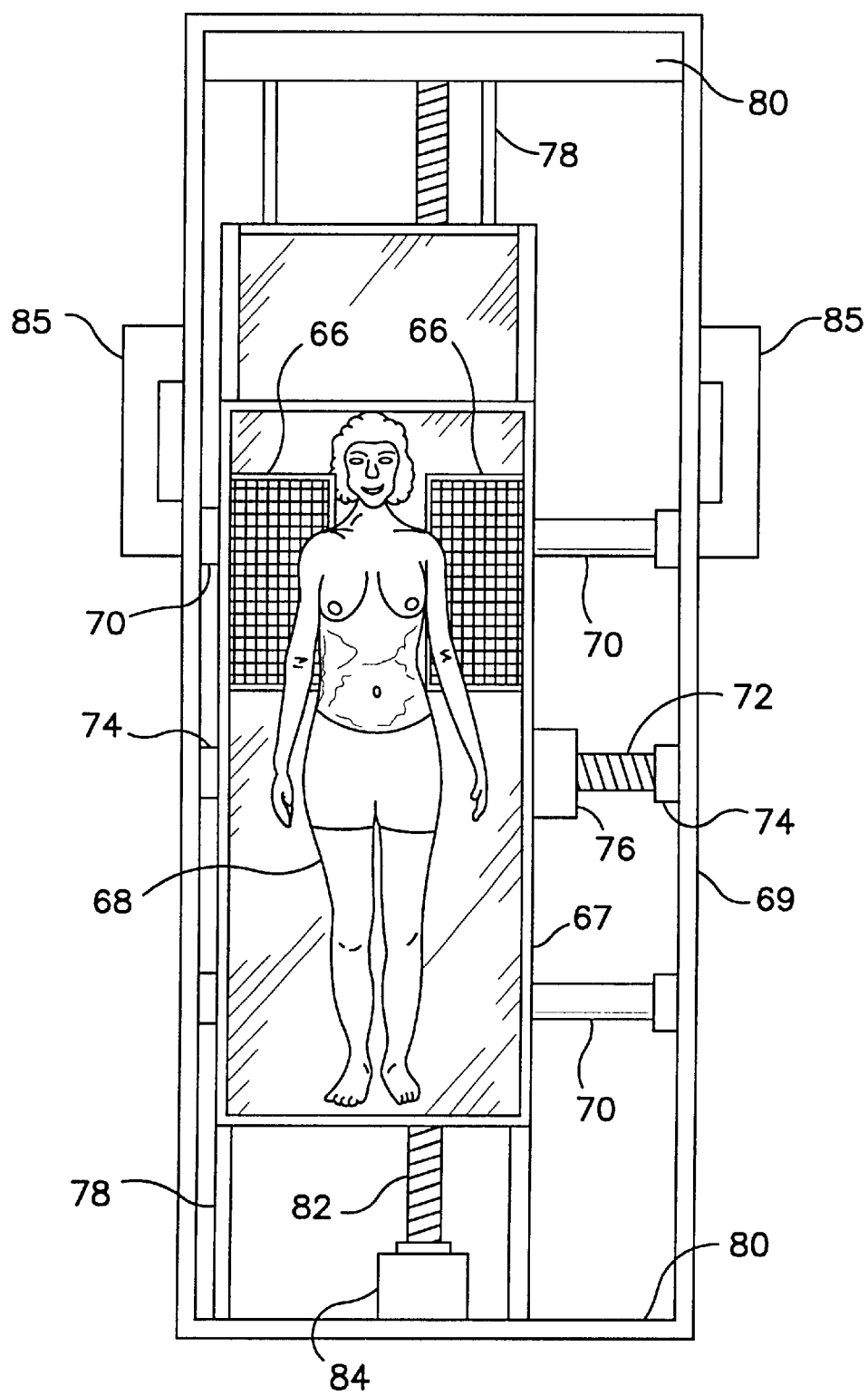
FIG. 2 is a schematic top plan view showing a patient positioned on the patient positioning bed.

In order to perform a complete breast examination, a person lies face-up on a bed 67 mounted on a position adjusting assembly 69 as seen in FIG. 2. The bed will be positioned generally below detection head 14 of FIG. 1.

Bed 67 has a comfortably padded upper surface, with matrix boards 66 adjacent to the shoulders of person 68. Conventional optical measuring means (not shown) can be provided to locate the exact position of arms, shoulders and neck relative to the matrix board 66 pattern during a first examination. Then, when the person 68 is again positioned on the bed 67 for a later examination, the optical system in conjunction with conventional software can again determine the person's position relative to matrix boards 66 and the position of the bed 67 can be adjusted in accordance with stored location information to place the person in substantially the identical position as for the first examination. Further, if person 68 were to move during the examination, the optical system can detect and correct for the change in position. It is highly desirable that the person 68 be positioned as identically as possible for each of the periodic examinations.

The underside of bed 67 includes conventional tubular bearings (not seen) through which horizontal guide rods 70 pass. A central threaded rod 72 engages end bearings 74 on assembly 69 and passes through a conventional motor driven nut assembly 76. As the motor driven nut assembly 76 is rotated in one direction or the other, bed 67 will be correspondingly moved sideways. Similarly, a pair of guide rods 78 extend between end walls 80 of assembly 69. Guide rods 70 and 78 are each arranged in a set of at least two parallel guide rods. A central threaded rod 82 passes through a conventional threaded block (not seen) secured to the underside of bed 67. A motor 84 rotates threaded rod 82 to move the bed 67 in either lengthwise direction, as desired. The overhead end blocks 26 and 28 (FIG. 1) are mounted on posts 85, the lower portions of which are seen in FIG. 2.

The operating structure of detection head 14 is detailed in schematic elevation view in FIG. 3. A removable connection 86 for main housing 87 mounts detection head 14 on arm 61. Preferably, detection head 14 is rotatable relative to arm 61 by a motor 88.

A detector housing 90 for palpation finger 92 and sensor 94 for sensing distance, color and temperature is mounted on main housing 87 through arms 96 and 98. Finger 92 is, designed to act like a physician's palpating finger in a manual breast examination. Typically, finger 92 will be formed from a sturdy, disposable material, such as glass.

Sensor 94 includes a distance measuring mechanism, of the sort used in cameras and the like, for providing precise distances between the breast surface and the sensor. If desired, a plurality of spaced range finders may be used to assure that palpation finger 92 is oriented perpendicular to the breast surface.

A conventional means for measuring the color of the breast surface being examined is included in sensor 94. Typically, this can be a conventional prism for breaking up incoming light and refracting each color of light to an independent photo electric or photo resistive sensor.

Palpation finger 92 is secured to a distal end of a shaft 100 that is slidable through housing 90 and pivoted at its proximal end to a distal end of arm 102 at pivot point 104. Arm 102 is rotatable about an axis 106 centrally located along arm 98. The proximal end of arm 102 is pivotally connected to drive shaft 108 at pivot point 110. When shaft 108 is moved axially by an actuator within actuator housing 112 (as detailed below in conjunction with the description of FIG. 4) shaft 100 and palpation finger 92 move a proportional distance in the opposite direction. As discussed below, a laser reader in reader housing 114 detects movement of shaft 108 and the feedback resistance to movement experienced by palpation finger 92 when pressing against breast tissue.

An error correction sensor 116 is provided on detector housing 90, cooperating with a member 119 mounted on shaft 100 to detect and correct positioning errors. It is possible that moving components of the detection head 14 mechanism shown in FIG. 3 may not be positioned correctly any time after coils 118 (FIG. 4) have been activated and repositioned. Resetting the position of the moving components, e.g., detection head 90, shaft 100, arm 102, and therefore palpation finger 92, is accomplished by the first coil 118 at the left as seen in FIG. 4. Slight changes in position of the breast skin, due to breathing or the like, is sensed by finger 92 and a corresponding position correction signal is sent to the leftmost coil 118 to correct for that displacement. While this precision is often not required, it is available if needed.

The internal components within actuator housing 112 and reader housing 114 are schematically illustrated in FIG. 4. A series of electromagnetic coils 118 are arranged in a uniformly spaced relationship along a central tube 120. An end shaft 122 is axially secured to the proximal end of shaft 108 and extends into tube 120. Shaft 108 slides in a sleeve 123.

End shaft 122 is formed from a magnetic material so that when coils 118 are actuated sequentially, beginning with the coil adjacent to the end shaft 122 fastened to shaft 108, the magnetic forces will tend to pull end shaft 122 into tube 120. As shown in FIG. 3, this pulls shaft 108, arm 102 and shaft 100 and pressing palpation finger 92 toward an adjacent breast.

The magnetic forces provide a rather "soft" pull so that breast tissue can stop the advance of palpation finger 92 without severe compression. The distance the finger advances will be in proportion to the density of the tissue, with a lump of more dense tissue resisting penetration, so the distance the finger advances will be less. This arrangement of arm 102, shafts 100 and 108 with magnetic coils 118 could be thought of as a weighing scale where breast tissue density corresponds to the object to be weighed and the magnetic actuator is the standard portion of weight placed on the other side of the scale.

In operation, the first coil of coils 118 will be actuated, moving palpation finger 92 a predetermined distance. Typically the coil is powered up stepwise, at about 250 mv per step up to about 10 volts maximum. The pressure change per step is typically only about 10 grams per mm 2 per step. If tissue resistance is low, the second coil of coils 118, and others in sequence, will be similarly actuated, further moving the finger 92. Eventually, tissue resistance will reach a predetermined level and the distance traveled by the finger 92 will be measured, as detailed below, and the information transferred to conventional information storage means.

The mechanism for encoding and transmitting the palpation information to the storage and use station (computer center 17) is enclosed in reader housing 114. As seen in FIG. 4, a conventional laser optic card 124, using technology as applied in musical compact disks but with a single straight track, is carried by shaft 108. A laser card reader 126 reads the shaft 108 position from the card 124 and transmits the encoded information to the information collection station. There, the information can be converted to machine language or any desired format for interpretation by conventional software systems of the sort used in CAT scan systems or other medical scanning systems. Any error or mechanical tilt is detected in real time by error correction sensor 116 that filters out any mechanical movement other than the desired palpation movement.

A typical laser card 127 of the sort used in reader 126 is schematically illustrated in FIG. 4a. Card 127 has a series of reflecting areas 129 separated by non-reflective areas 131. While non-reflecting areas 131 could be light absorbing, generally it is preferred that they be transparent so the incident light will pass through. A laser transmitter 133 directs a laser beam 135 against the patterned area of laser card 127. When the laser beam 135 hits a reflecting area 129, reflected light is picked up by a receiver 137. As card 127 is moved transversely, conventional software can count the pattern of reflected pulses to measure movement of shaft 108 and, ultimately, palpation finger 92. The reflecting areas 129 can be as small as about 0.001 mm for highly precise movement measurement.

An adjustment mechanism 128, such as a threaded adjustment shaft acting similar to a turnbuckle, is provided to adjust the position of shaft 108 relative to the array of electromagnetic coils 118. The maximum excursion of shaft 108 is limited by pin 130 extending from shaft 108 and limit switches 132.

The unit will thus sequentially test areas to provide a "picture" of the entire breast surface, revealing density changes indicative of tumors on a very fine scale, in a manner similar to the images produced in MRI, CAT and other physical scanning methods.

Figure 5:
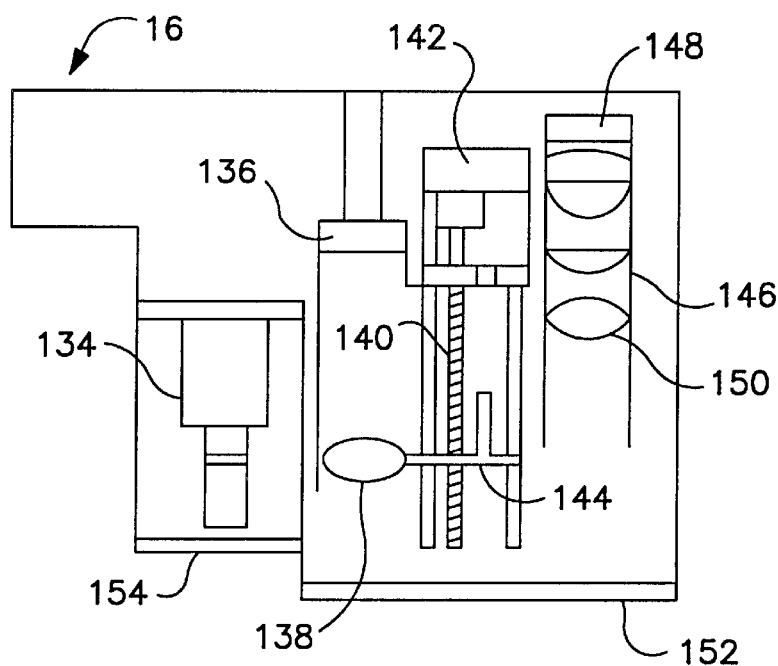
FIG. 5 is a schematic diagram of a first embodiment of a locator head assembly.

To provide the maximum consistency of results from one examination to the next, it is highly desirable that the person and the breasts be positioned as identically as possible for each examination. The movable bed arrangement shown in FIG. 2, in cooperation with the locator head 16 schematically illustrated in FIG. 5, provides accurate positioning by locating the position of a person 68 on the bed 67 and actuating the various carriage 10, bed 67 and detection head 14 movement mechanisms under computer control to locate the breast to be examined in substantially the same position it was in at the last prior examination.

A digital camera 134 provides a digitized image of the breast and patient in a matrix manner to supply sufficient data for the ongoing examination session and the prepositioning of the patient whenever a new image is required. A computer system can compare the original image to a subsequent image at the start of a subsequent examination so that the patient's position can be adjusted until the images match.

A white light source 136 is provided with a schematically illustrated focussing lens system including lens 138, a lead screw 140 rotatable by motor 142 and threaded through a lens mount bracket 144 to focus a light spot on the breast surface. As the spot of light is moved transversely and focussed at different depths along the breast, the scan can be saved in computer memory in a conventional manner to produce a three-dimensional image of the breast.

In addition, a laser scanner 146, including a laser emitter 148 and a focussing system 150 for producing a small spot on the breast being examined may be used in the same way as the white light spot to create a three-dimensional image. Typically, a 680–820 nm, 0.0095 mw laser may be used, since that laser has sufficient power for imaging without damaging the skin.

A window 152 of glass or plastic that is transparent to the white light and laser light closes the bottom of locator head 16. A similar window 154 covers the side of head 16 adjacent to camera 134.

The vertical support mechanism 18 for raising and lowering the entire carriage 10, as seen in FIG. 1, is illustrated in FIG. 6. Vertical guide rods 38 extend from a sturdy base 156 to a top plate 158. End blocks 26 and 28 carry horizontal support 12 (FIG. 1, omitted from FIG. 6 for clarity) for vertical movement therealong.

A powerful motor 160 rotates the sturdy lead screw 40 threaded through block 28. An upper limit switch 164 and a lower limit switch 166 prevent movement of horizontal support 12 beyond desired limits. For a very strong, sturdy assembly, base 156 will rest on the floor or a sub-floor so that bed assembly 67 could be positioned within a frame formed by base 156, top plate 158 and vertical guide rods 38.

The image produced by either of these light spots produced at a first examination can be compared to an initial image produced at a later examination to adjust the breast position to substantially match the original position. This will aid in re-examining a suspicious spot or lump found in the initial examination during later examinations.

The three-dimensional images can be divided into a matrix of cubes or slices with geometric indicia (e.g., a cube might be identified as cube 2,4,9 on an x-y-z axis basis) and location scan be directly compared between the light spot image and the finger palpation locations.

Figure 7:
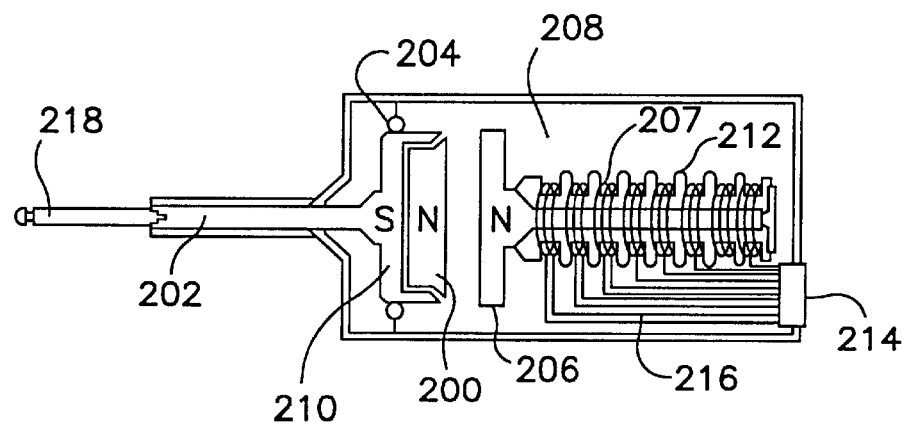
FIG. 7 is a schematic representation of the internal components of a first detection head embodiment.

A second embodiment of internal components of a detection head for detecting changes in density, hardness, and the like in breast tissue in as elected very small area is schematically illustrated in FIG. 7.

A permanent magnet 200 mounted on a non-magnetic rod 202 is movable along the axis of the rod 202 centerline. Suitable guides 204, such as rollers, ball bearings, a sleeve or the like, allows smooth, low resistance, axial movement of rod 202. Permanent magnet 200 faces an electromagnet head 206 mounted on a shaft 207 and fixed to housing 208. Poles of permanent magnet 200 and electromagnet head 206 (when activated) have the same poles juxtaposed, here having north poles adjacent to each other as indicated, with the electromagnet south pole at 210. Electromagnet head 206 is powered by any suitable number of powered coils 212, connected at terminal 214 to a power source via wires 216.

Since the magnets 200, 206 have the same poles opposite each other, the arrangement will tend to "push" the magnets apart as soon as electromagnet coils 212 are activated. The intensity of this "pushing" force can be varied in accordance with the number of turns in coil 212 and the power provided thereto.

Figure 11:
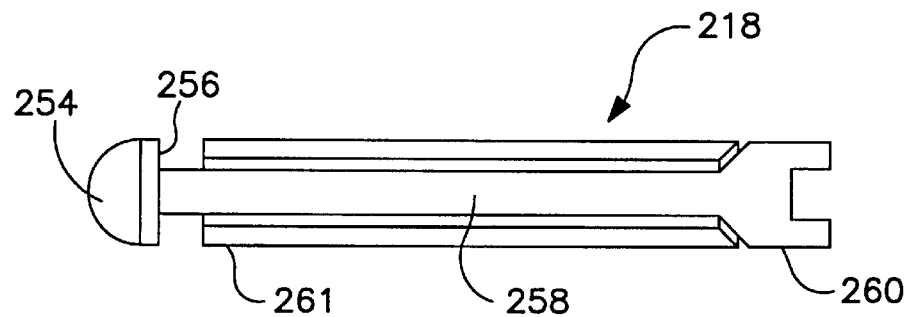
FIG. 11 is a schematic representation of a palpation tip for a detection head.

A palpation tip 218 (i.e., palpation finger 92), as detailed in FIG. 11, is mounted on the distal end of rod 202. Tip 218 is brought into contact with(or to a predetermined distance from) the breast surface by carriage 10 as described above. Coil 212 is energized to increase the field around shaft 207 to increase the field at electromagnet head 206 and force permanent magnet 200 further away from electromagnet head 206, which moves tip 218 against the breast. The breast tissue is depressed at the point of contact, with tissue elasticity pressing tip 218 and non-magnetic rod 202 back toward coil 206 in accordance with tissue elasticity and hardness at the contact point.

Figure 13A:
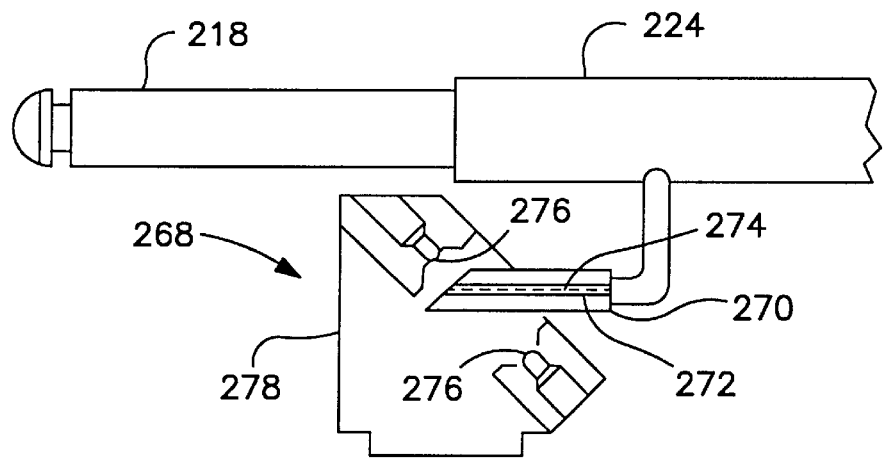
FIG. 13a is a schematic representation of one embodiment of an encoder slide assembly for palpation tip position measurement for use with a single tip arrangement or a multi-tip arrangement as seen in FIG. 12.
Figure 13B:
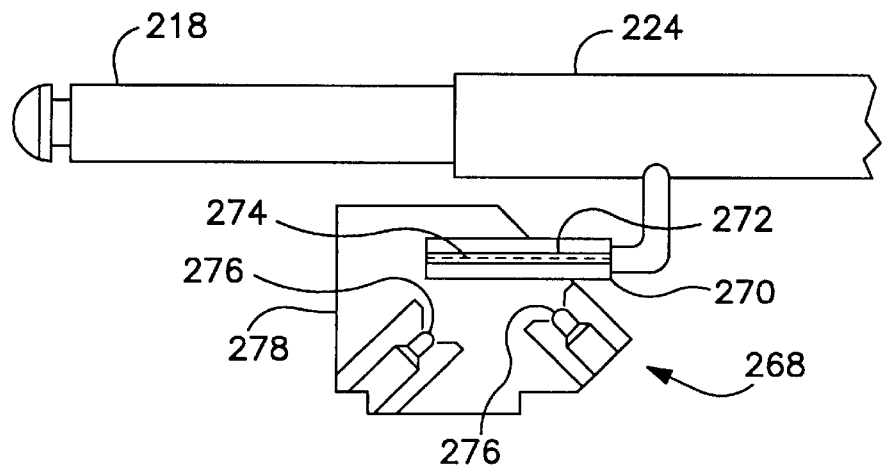

Variations in this back pressure as represented by the extent to which the tip presses into the breast tissue are transmitted to the recording instrumentation by any suitable means for measuring the movement of tip 218. Typically, the position of tip 218 may be measured by the mechanism shown in FIGS. 4 and 4a, as discussed above. Another embodiment of a tip 218 position measuring system is shown in FIG. 13, described below.

The resilient mounting of permanent magnet 200 resulting from the field between the two magnets 200, 206 will permit the permanent magnet 200, should it strike a breast or other surface during positioning of detection head 14, to provide sufficient "give" to prevent injury or damage to the breast or other surface.

Figure 8:
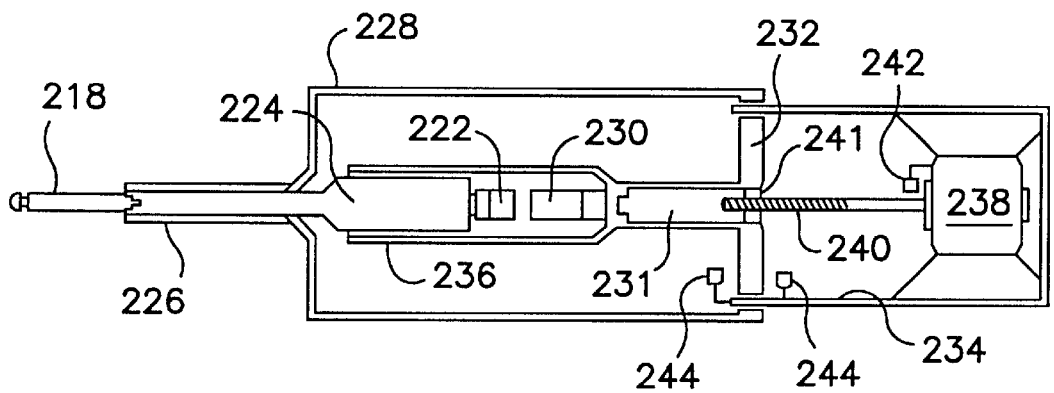
FIG. 8 is a schematic representation of the internal components of a second detection head embodiment.

Another embodiment of internal components of the detection head is illustrated in FIG. 8. A permanent magnet 222 is mounted on the proximal end of an actuator rod 224 which is slidable along a sleeve 226 mounted on housing 228. A tip 218 of the sort detailed in FIG. 11 is secured to the distal end of rod 224.

A second permanent magnet 230 is mounted on a holder 231 coaxial with rod 224. Same poles (north to north or south to south) on each of magnets 222 and 230 face and repel each other. Holder 231 is supported on a disk 232 slidable within housing 234 coaxial with rod 224. A sleeve 236 is preferably mounted on holder 231 to aid in guiding movement of rod 224.

Detection head 14 is moved as discussed above to bring palpation tip 218 into proximity with a selected location along the breast surface. When tip 218 is initially brought into proximity to the breast surface, rod 224 will hang down and the force of gravity will cause the rod to move to a point where the gap between magnets 222 and 230 will increase.

A motor 238 mounted in housing 234 drives a lead screw 240 which is threaded through a corresponding female thread 241 in disk 232. Motor 238 may be any suitable motor, such as a low rpm DC motor or a stepper motor. Rotation of lead screw 240 will move magnet 230 toward magnet 222 decreasing the intermagnet gap until breast resistance to penetration of tip 218 will return the intermagnet gap to a predetermined distance. The distance that holder 231 and disk 232 move is representative of breast density characteristics at the contact point. A conventional sensor 242 counts the revolutions of motor 238 to measure the corresponding degree of penetration of tip 218 into the breast.

Conventional safety sensors 244 may be provided to limit maximum movement of disk 232 (and movement of tip 218 in accordance with disk position) to prevent damage to the breast. As mentioned above, the magnetic field between magnets 222 and 230 will act as a resilient mount for tip 218, limiting damage or injury should the tip strike a breast or other surface.

Figure 9:
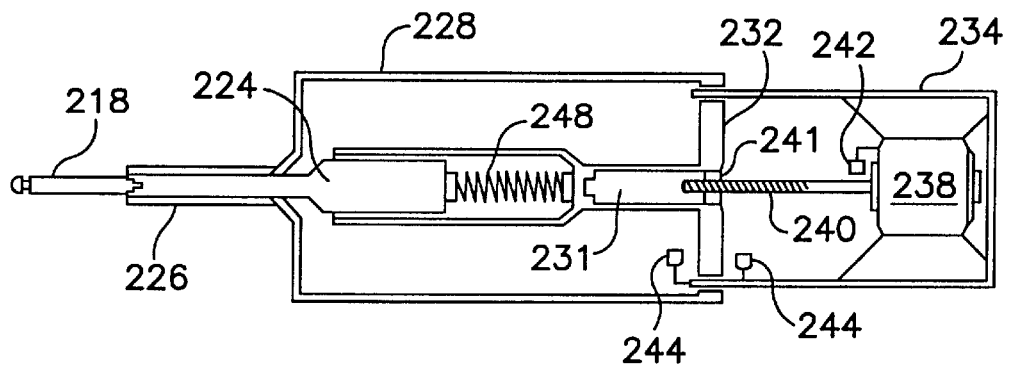
FIG. 9 is a schematic representation of the internal components of a third detection head embodiment.

FIG. 9 is a schematic diagram of another embodiment of detection head 14. Here, housings 228 and 234, actuator rod 224, sleeves 226 and 236, tip 218, holder 231, disk 232, motor 238 and sensors 242 and 244 are the same as shown in FIG. 8 and discussed above.

Instead of the spaced permanent magnets 222 and 230 used in the FIG. 8 embodiment, a spring 248 is fastened between the proximal end of rod 224 and holder 231. Spring 248 is selected to bias the two juxtaposed ends to a particular, predetermined spacing. As discussed in conjunction with FIG. 8, above, when the detection head 14 is positioned over a breast, tip 218 extends downwardly under the force of gravity. Motor 238 rotates to move disk 232 and holder 231 toward rod 224 until the gap between the distal end of holder 231 and the proximal end of rod 224 is at the original predetermined distance. The total movement of holder 231 is indicated by the number of revolutions of lead screw 240 as measured by counting sensor 242, which is indicative of breast tissue physical parameters.

Figure 10:
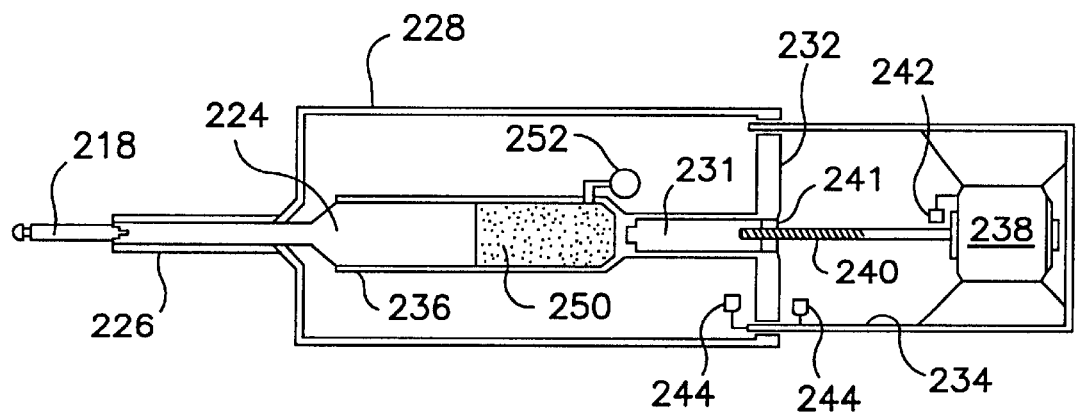
FIG. 10 is a schematic representation of the internal components of a fourth detection head embodiment.

Another embodiment of a detection head 14 is schematically illustrated in FIG. 10. Most components are the same as in the embodiments of FIGS. 8 and 9. However, here in place of a magnetic field or spring between the proximal end of rod 224 and the distal end of holder 231, a gas 250 is enclosed within sleeve 236 at the proximal end of rod 224. Sleeve 236 fits over rod 224 in a sealing arrangement to prevent pressurized gas 250 from escaping. Any suitable conventional seals may be used between rod 224 and sleeve 236.

Any axial physical force applied to rod 224 will change the gas pressure within sleeve 236 which will be measured by a conventional pressure sensor 252 capable of providing an electronic read-out. As before, when the tip 218 is aligned downwardly in contact with breast tissue, the pressure sensed will be lower. Lead screw 240 will be rotated by motor 238 to move holder 231 toward sleeve 236 to slide the sleeve 236 over rod 224, decreasing the volume and increasing pressure. The number of motor rotations, as counted by sensor 242, required to bring pressure up to a predetermined level is indicative of breast physical parameters, such as hardness and density.

A preferred palpation tip 218 configuration is schematically illustrated in FIG. 11. Tip 218 includes a rounded endpiece 254 which touches the breast surface. Any suitable material may be used, which should be disposable or washable. An end isolator 256, made up of a soft electrically insulating material prevents any static electricity discharge from the body from affecting the readings. A core member 258 connects endpiece 254 to base 260 which is secured in any suitable manner, such as threads, to rod 224. Side isolator 261 is generally tubular and is mounted on base 260 and spaced from core 258 to absorb any side impacts or sudden shakes.

Figure 12:
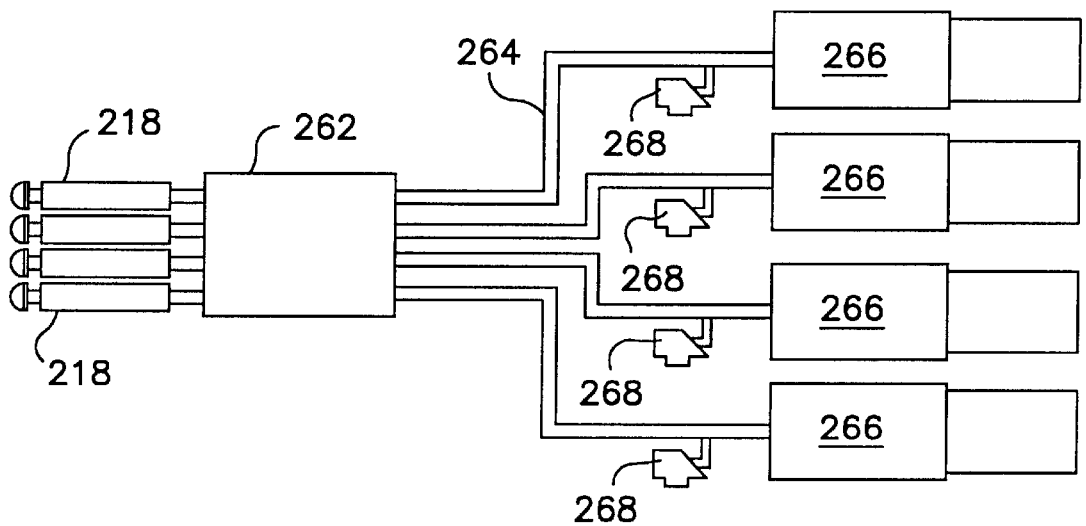
FIG. 12 is a schematic representation of a detection head having a plurality of parallel palpation tips.

FIG. 12 schematically illustrates a detection head 14 embodiment in which a plurality of tips 218 can be used in a closely spaced parallel array. Here, a plurality of tips 218, typically of the sort shown in FIG. 11, are mounted on actuator rods 262, typically rods similar to rods 224 described above, mounted for axial movement. Extension connectors 264, which may be rigid offset members of the sort schematically shown, inflexible cables, or the like, which are capable of transmitting motion from systems 266 of the sort shown in FIGS. 7–10, are connected between the output ends of rods 224 of those systems and tip 218 actuator rods.

An encoder slide is preferably included in each extension connector 264 to provide highly accurate readout of movement of each tip 218 during breast palpation. A preferred encoder slide assembly 268 is detailed in the schematic illustration of FIG. 13. Such an encoder slide assembly 268 may be used with any of the single tip arrangements of FIGS. 7–10.

As seen in FIG. 13, a preferred encoder slide assembly 268 includes an encoder slide 270 secured to rod 224, as schematically shown, for movement with that rod. Encoder slide 270 could be secured to any suitable part of rod 224 or to tip 218, as desired. Encoder slide 270 is transparent and includes a strip 272 bearing reflective dots 274 (or, in the alternative transparent dots in an otherwise opaque strip 272).

Decoder sensors 276 are provided on opposite sides of encoder slide 270, mounted on a housing 278 secured to housing 228 by any suitable mounting means. Decoder sensors 276 are optical or laser sensors and light emitters of the sort used with conventional music or computer compact disks.

Where dots 274 are reflective against a transparent background, light will pass from a light transmitting decoder sensor 276 to the other, which is a light detector. As encoder slide 270 moves, light will be reflected away when a reflective dot is present between the decoder sensors and will pass to the detector when a space between dots is present in the optical path. Thus, changes between receiving and not receiving light at the second decoder sensor will indicate movement of the slide and the number of pulses of light received during encoder slide 270 movement will indicate distance of movement of rod 224 and tip 218.

Where dots 274 are transparent against an opaque background, light pulses received at the detector decoder sensor 276 will indicate movement and distance of movement.

Figure 14:
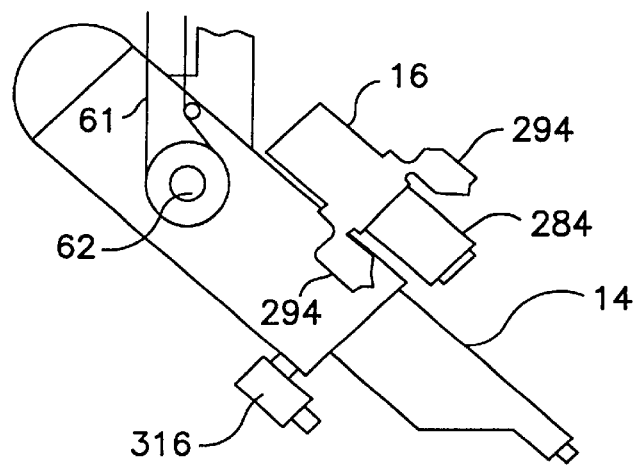
FIG. 14 is a schematic elevation view of a second embodiment of the distal end of the carriage shown in FIG. 1.

In the embodiment shown in FIG. 1, the optical locator head 16 is mounted separately from the arm 61 carrying the detection head 14 carrying the palpation finger 92 and sensor 94. FIG. 14 illustrates an alternate embodiment in which the optical locating head 16 and detection head 14 are both mounted at the end of the arm 61 on carriage 10.

Figure 15:
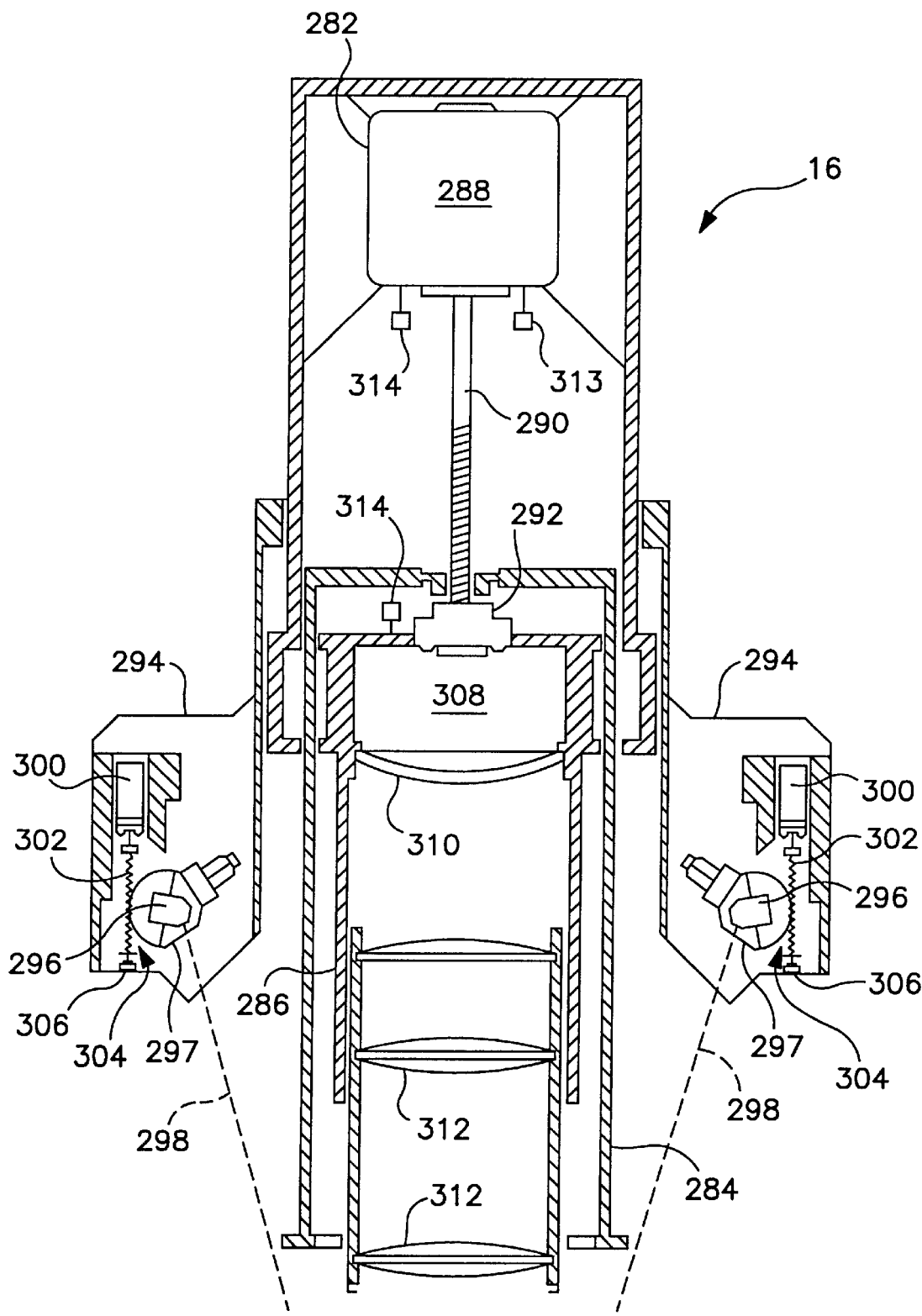
FIG. 15 is a schematic representation of the internal components of a second embodiment of a locator head assembly.

Optical locator head 16 in the FIG. 15 embodiment includes a motor housing 282 secured by any conventional means, such as bolts (not seen) to detection head 16. A lens enclosure 284 is secured to motor housing 282 after precise positioning during manufacture of the assembly. A lens assembly 286 is slidably mounted within lens enclosure 284 for axial movement relative thereto.

A motor 288 is mounted within motor housing 282 and drives a lead screw 290 which is threaded through a nut 292 secured to lens assembly 286 to move the lens assembly 286 axially within lens enclosure 284.

Two laser beam positioning enclosures 294 are mounted on opposite sides of motor housing 282. Each enclosure 294 contains a pre-focussed conventional visible light (typically 680 to 850 nanometer) laser diode and light sensor unit 296. A prism 297 refracts light from the laser diode in unit 296 toward the breast being examined, typically along schematically indicated light beams 298. Light reflected from the breast surface passes back through prism 297 to the sensor in unit 296. This diode and sensor unit 296 operates in the same manner as conventional compact disk readers. The sensed returned light will be maximum when the beam from the beam generated by unit 296 is 90° to the breast surface. The mechanism described above for moving palpation tip 218 in three dimensions can thus adjust tip orientation to provide palpation at 90° to the breast surface. Two enclosures 294 with the components described above are preferably provided, with the first used to palpate one breast and the second used to palpate the second breast, since the size and shape of the two breasts are often somewhat different.

A motor 300 in each of the laser beam positioning enclosures 294 drives a lead screw 302 that engages an arcuate gear sector 304 to rotate each unit 296 and prism 297 about a center of rotation of the gear sector 304. Prism 297 preferably refracts light from the diode in unit 296 at 90°. The laser diode within unit 296 generates a laser beam that produces a red dot on the breast being examined. A conventional sensor 306 within each enclosure 294 counts rotation of lead screw 302 and is calibrated to indicate the exact distance to the surface upon which the dot appears when the beam is 90° to the surface. The system computer then can conventionally calculate a three dimensional image of the breast surface from a number of these angle readings.

Lens assembly 286, in conjunction with a light sensor 308, a pre-focussed sensor lens 310 and lenses 312 operate in the same manner as conventional camera automatic focussing systems to bring the breast surface into sharp optical focus by rotating lead screw 290 as necessary. A position sensor 313 counts rotation of lead screw 290 to provide information to the central computer as to the position of focus. Since optical locator head 16 moves in conjunction with detection head 14, when locator head 16 is moved to focus on the breast surface, palpation tip 218 will be brought into the predetermined contact with the breast tissue.

Extreme position sensors 314 are preferably provided to sense movement of lens enclosure 284 to the ends of its desired range of movement and prevent damage which might be caused by movement outside the selected range. Sensors 314 may be any conventional sensors, such as pressure switches, which can turnoff motor 288.

In operation, either of the locator head 16 embodiments as shown in FIGS. 5 or 15 can be conventionally programmed to map an entire breast step by step. The horizontal and vertical (X and Y) movement of the carriage 10 takes locator head 16 to all of the selected points across the breast. The focussing mechanism within motor housing 282 and lens enclosure 284 will continually focus sensor 308 to provide the necessary Z direction alignment. The position sensor 313 will count the revolution of motor 288 while the motor is bringing lens assembly 286 to the point of focus to continuously provide lens position information.

Once locator head 16 has visited all desired points on the breast and has calculated its distance from every visited point, the computer can provide a conventional drawing in three dimensions of the entire breast. During palpation of the breast, location head 16 verifies the address being palpitated. Also, location head 16 will automatically compensate for breast movement as the patient breathes. If desired, a video camera 316 may be mounted on locator head 16, as seen in FIG. 14, to provide a general view of the breast during palpation.

Thus, the apparatus of this invention will provide an accurate map of the breast, will detect tissue density anomalies and will accurately re-examine the breast from time to time to monitor any changes in breast density anomalies.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

What is claimed is:

1. A location head for use with an apparatus for detecting small breast anomalies, which comprises:
   a first housing having an open end;
   a second housing slidably moveable into and out of said open end;
   means for moving said second housing into and out of said open end;
   an automatic focussing optical system in said second housing for achieving optical focus at a surface spaced from said optical system;
   said automatic focussing optical system comprising means for moving said optical system to achieve said optical focus and means for measuring movement of said optical system;
   at least one laser diode unit for projecting a laser beam onto said surface to produce a light dot; and
   means for adjusting said laser beam to an angle of about 90° to said surface including means for sensing maximum reflected light intensity.

2. The location head according to claim 1 wherein said means for moving said second housing comprises a motor secured in said first hosing, a lead screw rotatable by said motor, and a nut fixed to said second housing for receiving said lead screw and for moving along said lead screw to move said second housing.

3. The location head according to claim 2 further including sensor means for counting revolutions of said lead screw whereby position of said second housing can be continuously monitored.

4. The location head according to claim 2 further including limit switches for detecting movement of said second housing to predetermined maximum movement into and out of said first housing and preventing further such movement.

5. The location head according to claim 1 wherein said means for adjusting said laser dot positions comprises means for mounting said laser diode unit for rotation about a predetermined axis, a rotatable lead screw engaging a gear sector said laser diode unit and means for rotating each lead screw, whereby rotation of each lead screw will rotate said engaged gear sector to move said laser dot position along said surface.

6. The location head according to claim 5 wherein said means for rotation of each said lead screw comprises motor means for rotating said lead screw and means for counting revolutions of said lead screw whereby the position of the laser light dots and the angle between said laser light dots can be determined.

7. A location head for use with an apparatus for detecting anomalies in breast tissue, comprising:
   a. at least one light emitting unit that projects a light beam onto a breast surface;
   b. at least one light receiving unit for receiving the light beam as reflected off the breast surface;
   c. an automatic light beam positioning system to adjust the light emitting unit to a desired beam location whereby the light beam is aligned to a predetermined angle relative to the breast surface;
   d. an automatic optical focussing system that aligns at least one lens to a desired lens location whereby the at least one lens is in optical focus with the breast surface; and
   e. a sensing system that measures and transmits positional data regarding the desired beam location and the desired lens location whereby a detection head can be positioned on the breast surface to detect anomalies in breast tissue, an image of the breast can be produced and a map of the breast can be developed providing for subsequent, comparable breast anomaly examinations.

8. The location head of claim 7, wherein the light emitting unit further comprises a prism to refract light emitted from a source within the light emitting unit onto the breast surface.

9. The location head of claim 7, further comprising a camera to record images of the breast surface during palpation.

10. The location head of claim 7, wherein the light emitting unit and the light receiving unit are included in one device.

11. The location head of claim 10, wherein the light beam is a laser.

12. The location head of claim 11, wherein the focussing system is automatic and the at least one lens is aligned into optical focus by a lead screw rotatable by a motor.

13. The location head of claim 12, wherein the sensing system measures one dimension of the desired lens position by determining the number of rotations of the lead screw to calculate a distance that the desired lens position is located relative to the breast surface.

14. The location head of claim 11, wherein two combination laser emitting and receiving units are employed, a first combination laser emitting and receiving unit projecting and receiving a light beam on a surface of one breast and a second combination laser emitting and receiving unit projecting and receiving a light beam on a surface of a second breast.

15. A location head for use with an apparatus for detecting anomalies in breast tissue, comprising:

a. at least one light emitting unit that projects a light beam onto the breast surface;

b. at least one focussing system including at least one lens adjustable to a desired lens position whereby the light beam is focussed on the breast surface; and c. at least one sensing unit that measures and transmits the position of the desired lens position, whereby a detection head can be positioned on the breast surface to detect anomalies in breast tissue, an image of the breast can be produced and a map of the breast can be developed providing for subsequent, comparable breast anomaly examinations.

16. The location head of claim 15, further comprising a camera to record images of the breast surface during palpation.

17. The location head of claim 15, wherein the light beam is white light and one light emitting unit is employed.

18. The location head of claim 17, wherein the focussing system is automatic and includes one lens and a lead screw rotatable by a motor.

19. The location head of claim 18, wherein the sensing system measures one dimension of the desired lens position by determining the number of rotations of the lead screw to calculate a distance the lens is located relative to the breast surface.

20. The location head of claim 15, wherein the light beam is a laser and one light emitting unit is employed.

21. The location head of claim 20, wherein the focussing system is automatic and includes at least one lens to focus the laser beam, the at least one lens rotatable by a motor.

22. The location head of claim 21, wherein the sensing system measures one dimension of the desired lens position by determining the number of rotations of the lead screw to calculate a distance the lens is located relative to the breast surface.

* * * * *